(12) United States Patent
Vivenzio

(10) Patent No.: US 6,213,937 B1
(45) Date of Patent: Apr. 10, 2001

(54) TOOLLESS LIGHT PIPE MOUNT FOR LARYNGOSCOPE AND METHOD FOR RELEASABLY ATTACHING

(75) Inventor: Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/621,093

(22) Filed: Jul. 21, 2000

(51) Int. Cl.[7] .................................................. A61B 1/267
(52) U.S. Cl. ........................................... 600/199; 600/193
(58) Field of Search .................................. 600/185, 187, 600/193, 190, 199, 213, 245

(56) References Cited

U.S. PATENT DOCUMENTS

| | | |
|---|---|---|
| 4,958,624 | 9/1990 | Stone et al. . |
| 5,060,633 | 10/1991 | Gibson . |
| 5,529,570 | 6/1996 | Storz . |
| 6,013,026 | 1/2000 | Krauter et al. . |

*Primary Examiner*—Jeffrey A. Smith
(74) *Attorney, Agent, or Firm*—Wall Marjama & Bilinski

(57) ABSTRACT

A laryngeal blade assembly for a laryngoscope includes a light pipe assembly releasably attachable to a blade, the light being disposed along a major dimension of the blade. The light pipe assembly includes a support which fixedly retains the light pipe, the support further including a bore sized for receiving a non-axially disposed engagement member of the blade. The bore includes a first receiving cavity which is sized to receive the engagement member and a contiguous second receiving cavity having a slotted portion sized to receive only an undercut portion of the engagement member. The support can be axially shifted between the first and the second contiguous cavities to effect attachment and release of the light pipe assembly in a toolless fashion.

13 Claims, 4 Drawing Sheets

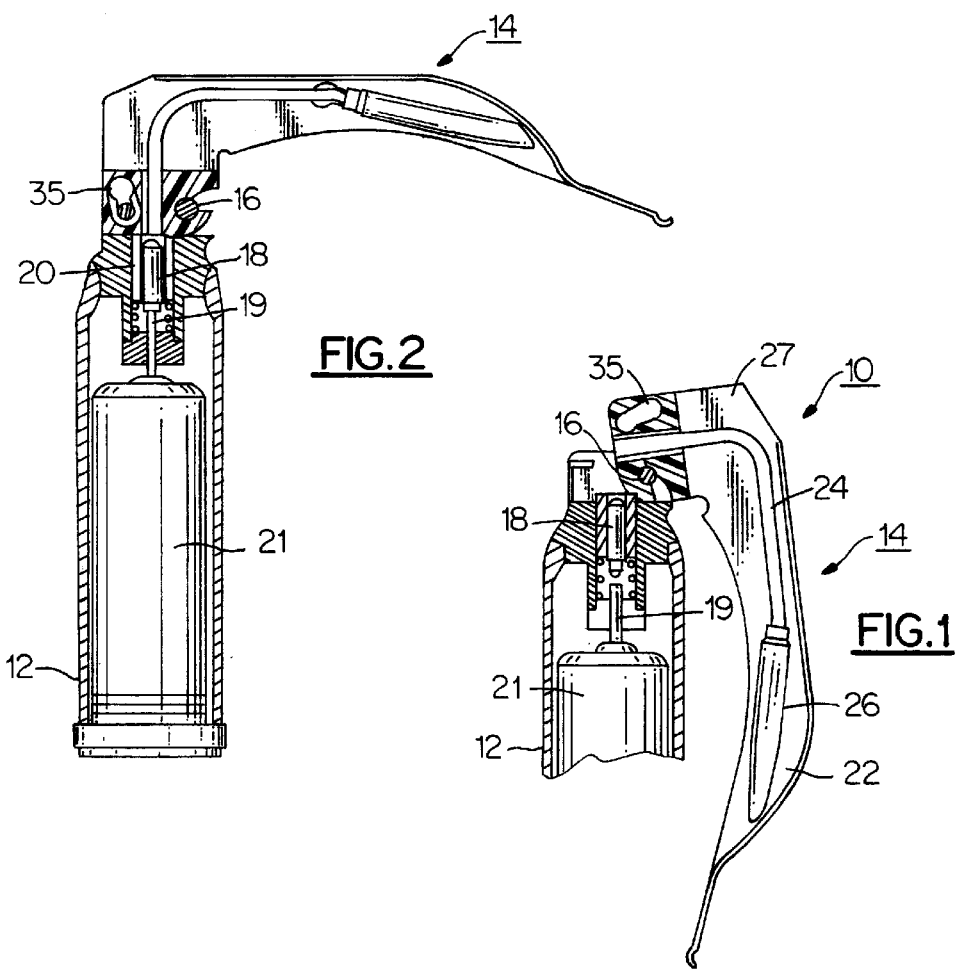
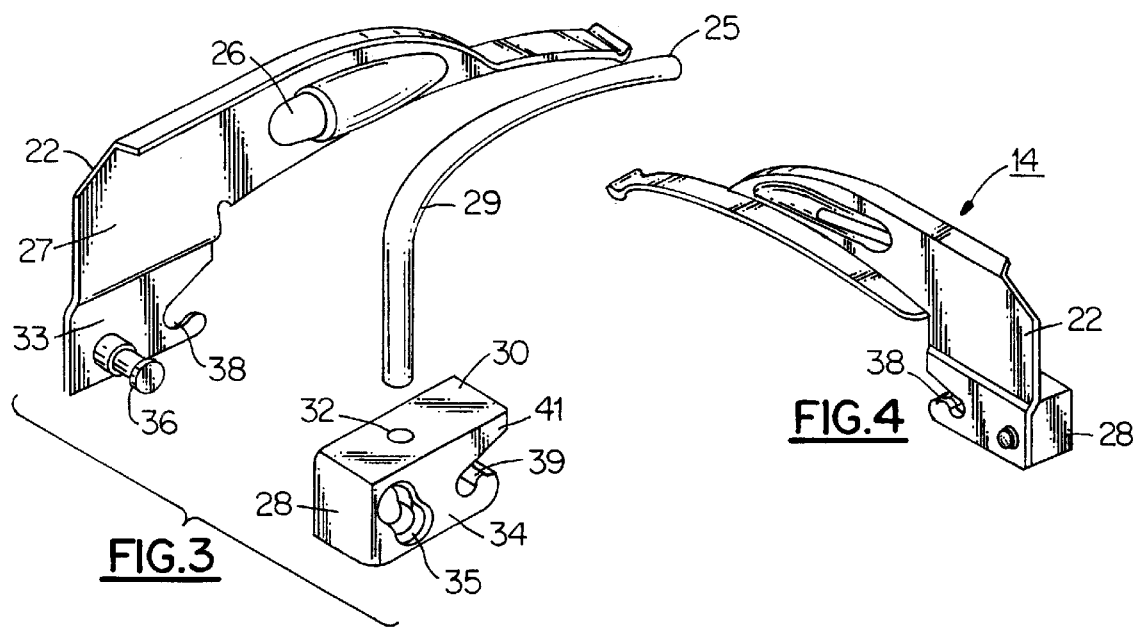

TOOLLESS LIGHT PIPE MOUNT FOR LARYNGOSCOPE AND METHOD FOR RELEASABLY ATTACHING

FIELD OF THE INVENTION

This invention relates generally to the field of laryngoscopes, and specifically to a hand-held laryngoscope having a removable blade assembly.

BACKGROUND OF THE INVENTION

As is known, laryngoscopes are medical diagnostic instruments used to displace the tongue and epiglottis to permit a direct view of the larynx in the introduction of tracheal tubes during intubation, narcosis and other life-threatening situations.

Most laryngoscopes consist of a handle containing at least one battery used as a power source. A pivotable laryngeal blade assembly extends from an upper portion of the handle, the blade being pivotable to permit the blade to fold substantially flat against the handle for storage or to a deployed position for use thereof. Furthermore, the blade assembly is completely detachable from the handle.

At least two general types of laryngoscopes are presently known. In one version, the handle interior contains a miniature incandescent lamp and a bundle of optical fibers, defining a light pipe, guides illumination from the contained lamp to the distal end of the blade. According to a second version, a miniature lamp is not provided within the handle, but rather is disposed at the distal end of the light pipe. In each version, the light pipe is attached to the blade.

It is often desirable that the light pipe be removed from the laryngeal blade assembly to allow for cleaning, disinfecting, and sterilization.

It is a further desire to be able to remove the light pipe from the laryngeal blade assembly without the use of tools. For example, U.S. Pat. No. 4,958,624 to Stone et al. describes a light pipe assembly which is mounted to a laryngeal blade using a removable threaded fastener, requiring that a screwdriver or similar tool be utilized to effect disassembly. This removal procedure, given the totality of situations in which a laryngoscope can be used, can be both tedious and time consuming.

Another known instrument which is commercially available from Heine, Inc. of Germany includes a laryngeal blade having a light pipe assembly which releasably slides onto the blade in an axial direction; that is, the light pipe assembly is attached and released along the major dimension of the blade. A problem with this particular design is that the light pipe assembly may be prematurely ejected due to a sudden impact such as might occur if the blade were to be inadvertently dropped. It is also conceivable that the light pipe may also be prematurely ejected during assembly to the handle. Due to the urgency of use of these instruments in an operating theater, emergency room, or similar location, an inadvertent release of the light pipe assembly is obviously not desirable.

A second toolless version is described in a recently issued and commonly assigned U.S. Pat. No. 6,013,026 to Krauter et al., the entire contents of which are herein incorporated by reference. As described therein, according to a supporting block fixedly retains a light pipe. The supporting block includes a bore disposed in a direction which, when assembled to the blade assembly, is substantially perpendicular to the major dimension of the blade. A projecting engagement member of the blade engages the bore of the supporting block, the engagement member further including an undercut portion and an annular engagement member fitted within the undercut. When engaged together, the annular engagement member retains the light pipe within the laryngeal blade assembly until a predetermined holding force is exceeded.

SUMMARY OF THE INVENTION

It is a primary object of the present invention to provide a laryngeal blade assembly that overcomes the above-described deficiencies of the prior art.

It is another primary object of the present invention to provide a laryngeal blade assembly which can be easily detached from the remainder of the blade assembly without the use of tools.

It is yet a further object of the present invention to provide a light pipe assembly which permits selective detachment from the laryngeal blade assembly, but in which the light pipe assembly remains relatively secure to the blade and instrument handle when dropped or subjected to a jarring impact.

It is still a further object of the present invention to provide a laryngeal blade assembly that can be used with either an incandescent lamp and/or a fiberoptic type laryngoscope.

Therefore, and according to a preferred aspect of the present invention, there is provided a blade assembly for a laryngoscope comprising a laryngeal blade configured for viewing the larynx of a patient and a light pipe assembly releasably attachable to the laryngeal blade. The light pipe assembly includes a supporting block for supporting the light pipe, the supporting block having an elongated bore for receiving an engagement member of the laryngeal blade in which the elongated bore includes a pair of contiguous receiving cavities, a first receiving cavity sized for initially engaging the supporting block and a second receiving cavity having a slot which substantially locks the light pipe assembly into place on the blade.

The engagement member is defined by a cylindrical shaft having an undercut portion. The first receiving cavity of the bore provided in the supporting block has a diameter which is sized to receive the diameter of the cylindrical shaft while the second contiguous cavity includes a slot sized only to receive the diameter of the undercut portion.

According to another preferred aspect of the invention, there is disclosed a hand-held laryngoscope for the examination of the larynx comprising a handle, a laryngeal blade attachable to said handle; and a light pipe assembly attachable to said laryngeal blade such that a light pipe is disposed along a major dimension of said blade. The light pipe assembly includes a supporting block for fixedly retaining said light pipe, said supporting block having a bore which is disposed non-axially with respect to a major dimension of said laryngeal blade. The bore is sized for receiving an engagement member of the blade and includes a first receiving cavity for initially receiving the engagement member and a contiguous second receiving cavity having a slot sized for releasably attaching the light pipe assembly to the laryngeal blade.

According to yet another preferred aspect of the invention, there is disclosed a method for releasably attaching a light pipe assembly to a laryngeal blade, said method including the steps of:

engaging a projecting member of the laryngeal blade with a bore of a supporting block of said light pipe assembly sized for receiving said member, said bore including a pair of contiguous receiving cavities and in which the projecting member is engaged with a first receiving cavity; and sliding the supporting block to align the projecting member with the second contiguous cavity of the bore to releasably lock the light pipe assembly to the blade.

An advantage of the present invention is that the light pipe assembly can easily be attached or detached from a laryngeal blade assembly without requiring tools while still maintaining a reliable connection therewith.

Another advantage of the present invention is that the light pipe assembly can be fitted by simply aligning the projecting member with the bore of the supporting block and using only finger pressure to complete the assembly. As such, the entire assembly and disassembly process can be completed using one hand.

These and other objects, advantages and features will be described in the following Detailed Description which should be read in conjunction with the accompanying drawings.

BRIEF DESCRIPTION OF THE DRAWINGS

FIG. 1 is a partial sectional view of a fiberoptic laryngoscope having a pivotable laryngeal blade assembly in accordance with the present invention, the blade being shown in a folded position;

FIG. 2 is a sectional view of the laryngoscope of FIG. 1 in a deployed or use position;

FIG. 3 is an exploded perspective view of the laryngeal blade assembly of FIGS. 1 and 2;

FIG. 4 is an assembled rear perspective view of the laryngeal blade assembly of FIGS. 1–3;

DETAILED DESCRIPTION

Figure 5:
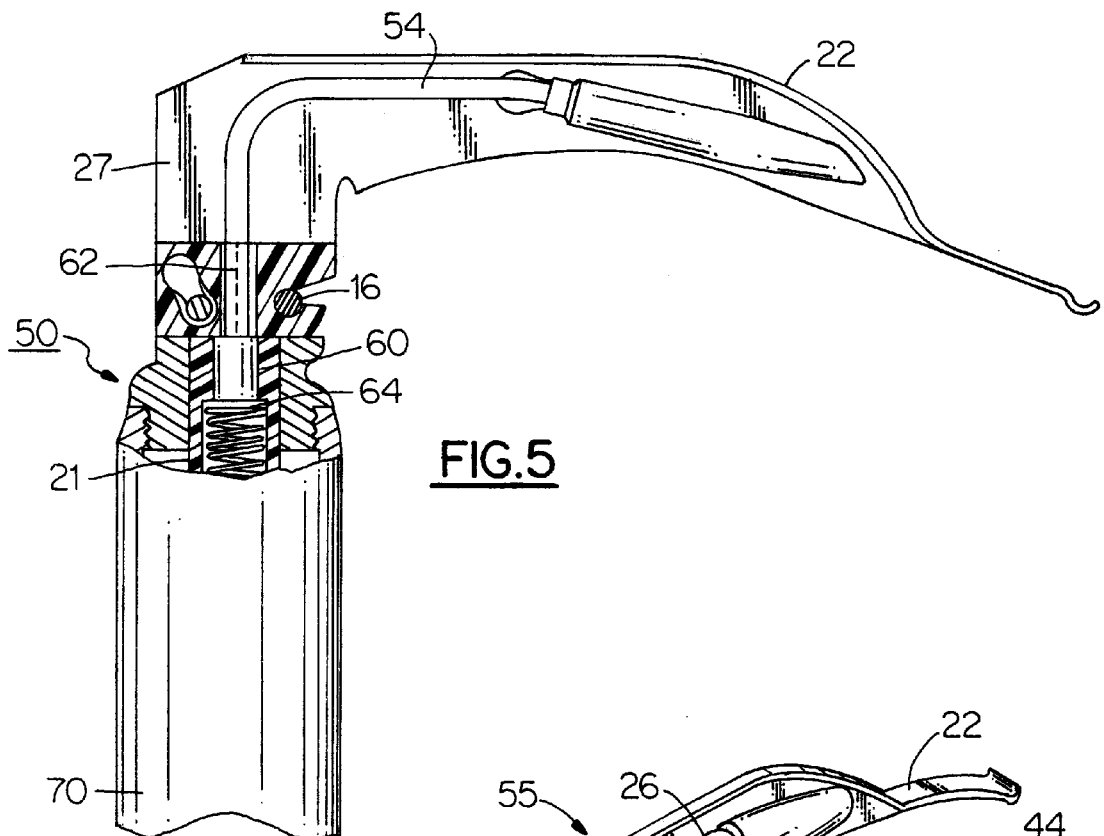
FIG. 5 is a partial sectional view of a conventional, standard incandescent lamp-type laryngoscope having a laryngeal blade assembly made in accordance with the present invention.

Before discussing that which Applicant regards as the main features of the present invention, a discussion of the two primary types of laryngoscopes is herein provided for background purposes. In brief, the first type of laryngoscope (also herein referred to as "the fiberoptic laryngoscope") and discussed with reference to FIGS. 1–4, includes a fiberoptic light pipe assembly, while the second type of instrument (also herein referred to as "the incandescent lamp laryngoscope") discussed with reference to FIGS. 5–7 includes a blade assembly which includes both a light pipe assembly having a contained miniature incandescent lamp. Each type of laryngoscope commonly includes a handle and a laryngeal blade assembly. It should be noted, however, that the handle of the first type of laryngoscope is not interchangeable with the handle of the second type of laryngoscope. In addition, each of the following embodiments is herein described using a MacIntosh-type blade assembly, though it will be readily apparent to one of sufficient skill that other blade designs, such as Miller blade assemblies among others, can easily be substituted using the inventive concepts described herein.

More specifically and referring to FIG. 1, the fiberoptic laryngoscope 10 includes a handle 12 and a laryngeal blade assembly 14 which is mounted on the upper portion of the handle about a pin 16 which is held in an operative position (see FIG. 2) by a latch (not shown). Slidably mounted in a tube 20 provided in an upper portion of the handle 12 is a miniature incandescent lamp 18. The lamp 18 is disposed in relation to a battery contact 19 which electrically connects the lamp to a contained battery power source 21. Movement of the laryngeal blade assembly 14 into the folded position of FIG. 1 releases the miniature lamp 18 from electrical connection with the contact 19, causing the lamp to de-energize. In order to energize the miniature lamp 18, the laryngeal blade assembly 14 is moved to its operative position (FIG. 2) which axially depresses the lamp 18 into intimate engagement with the battery contact 19. Additional details relating to the interrelations between the handle and blade assembly are found in U.S. Pat. No. 4,958,624 to Stone et al., the entire contents of which are herein incorporated by reference.

Referring to FIGS. 1, 3 and 4, the blade assembly 14 consists of a blade 22, sometimes referred to as a spatula, which is usually made from a stainless steel or other easily sterilizable material and a fiberoptic light pipe assembly 24 which is mounted in a receiving pocket 26 formed in an interior wall 27 of the blade 22. The blade 22 is shaped to permit passage into the throat and examination of the larynx, the blade further including a recessed proximal portion 33 having a projecting engagement member 36. The engagement member 36 extends in a direction which is substantially perpendicular to the major dimension of the blade 22.

Referring to FIGS. 1–4, the light pipe assembly 24 consists of a narrow cylindrical light pipe 29 and a supporting block 28 formed into a unitary subassembly, as shown in FIG. 3. The light pipe 29 is bent into a generally right-angled shape and is hollow to permit the passage therethrough of a plurality of optical fibers (not shown) that are used to transmit light from the miniature lamp 18 disposed within the handle 12 to a distal end 25 of the light pipe 29.

Figure 11:
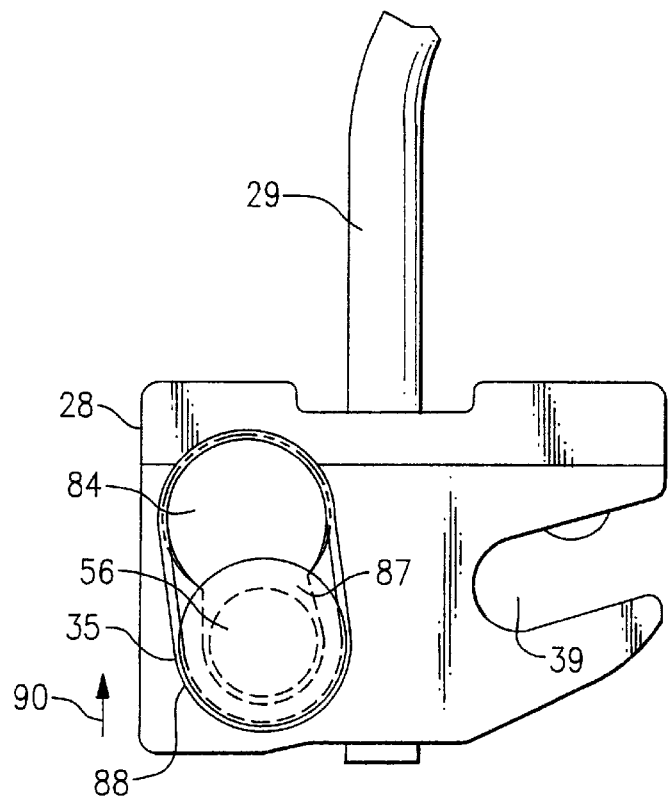
FIG. 11 is an enlarged partial side elevational view of the laryngeal blade assembly following initial attachment of the light pipe assembly.
Figure 12:
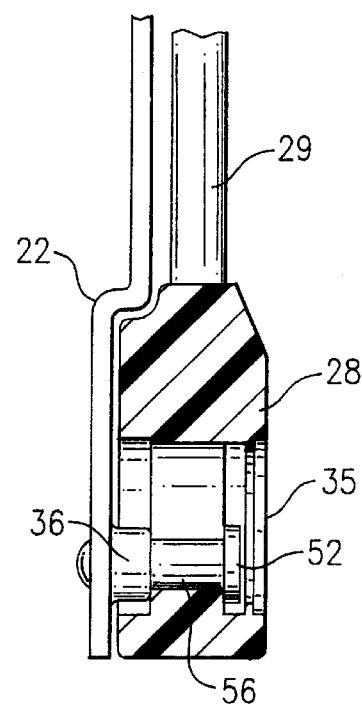
FIG. 12 is a sectional view of the assembly shown in FIG. 11.

The supporting block 28 includes a top surface 30 having an opening 32 which fixedly receives the other or proximal end of the light pipe 29. A bore 35 disposed through the side of the supporting block 28 is sized for receiving the projecting engagement member 36 of the blade 22 with the supporting block being fitted within the recessed proximal portion 33. The bore 35 includes a pair of contiguous receiving cavities 84 and 88, FIG. 11, to provide locking engagement. Salient features relating to the interconnection of the light pipe assembly 24 to the blade assembly 14 are described in greater detail below.

Figure 7:
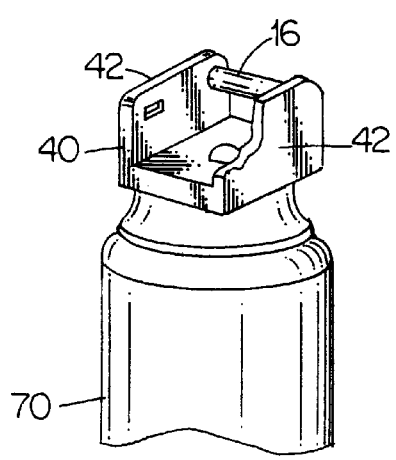
FIG. 7 is a partial perspective view of the laryngoscope of FIG. 1, illustrating an interlocking mount on the handle for receiving the laryngeal blade assembly of FIG. 6.
Figure 8:
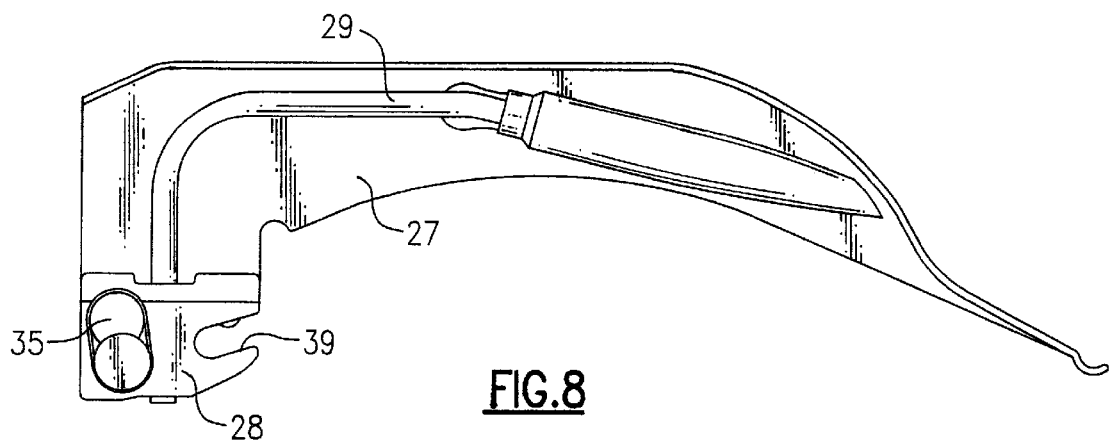
FIG. 8 is an elevated view of the laryngeal blade assembly of FIG. 1.
Figure 9:
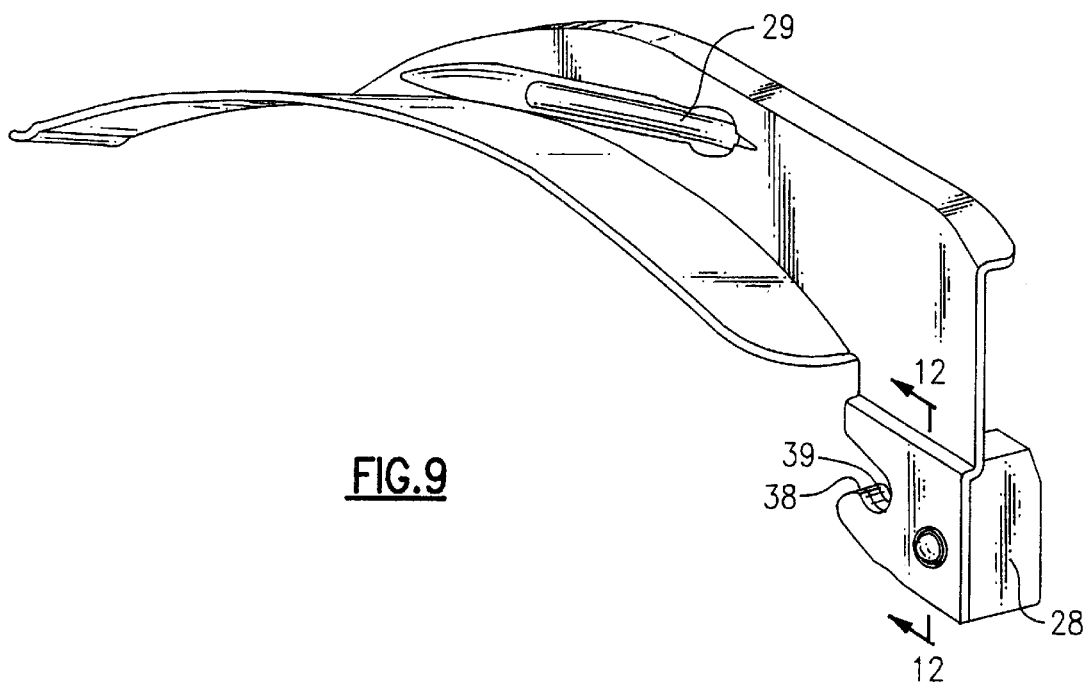
FIG. 9 is a side perspective view of the laryngeal blade assembly of FIG. 8.

Referring briefly to FIGS. 3, 4, and 7, the supporting block 28 further includes a base portion 37 and an elongated tongue 41 extending from one end. A slot 39 cut into the base portion 37 is sized to fit onto the pin 16 which is provided within a mounting bracket 40, shown most clearly in FIG. 7, in the upper portion of the handle 12. A similar slot 38 is defined in the recessed proximal portion of the blade 22 for fitting to the pin 16. The mounting bracket 40 is defined by a pair of side walls 42, defining a spacing 43 therebetween.

The width of the supporting block 28 is chosen such that when mounted on the blade 22, the overall combined width of the blade 22 and the supporting block will fit within the spacing 43 between the side walls 42 of the mounting bracket 40, FIG. 7. The mounting bracket 40 can be sized to fit either a fiberoptic or incandescent-type laryngeal blade assembly depending on the handle. As shown in FIGS. 1, 2 and 7, the sides of the mounting bracket 40 are spaced in accordance with ASTM F965, ASTM F1195, ISO7376-1, ISO7376-3 and EIN 1819 standards to receive the assembly defined by the blade 22 and the supporting block 28.

Thus and in operation, the described laryngeal blade assembly 14 will smoothly and snugly fit within the mounting bracket 40 when raised to the operative position shown in FIG. 2 and will force the lamp 18 into contact with the battery contact 19 in order to illuminate the lamp. The light from the miniature lamp 18 is then transmitted via the bundle of optical fibers (not shown) provided in the hollow light pipe 29 to the distal end 25 thereof to allow the desired target to be illuminated. With the laryngeal blade assembly 14 in the folded position of FIG. 2, the lamp 18 is deenergized in the manner previously described.

Figure 6:
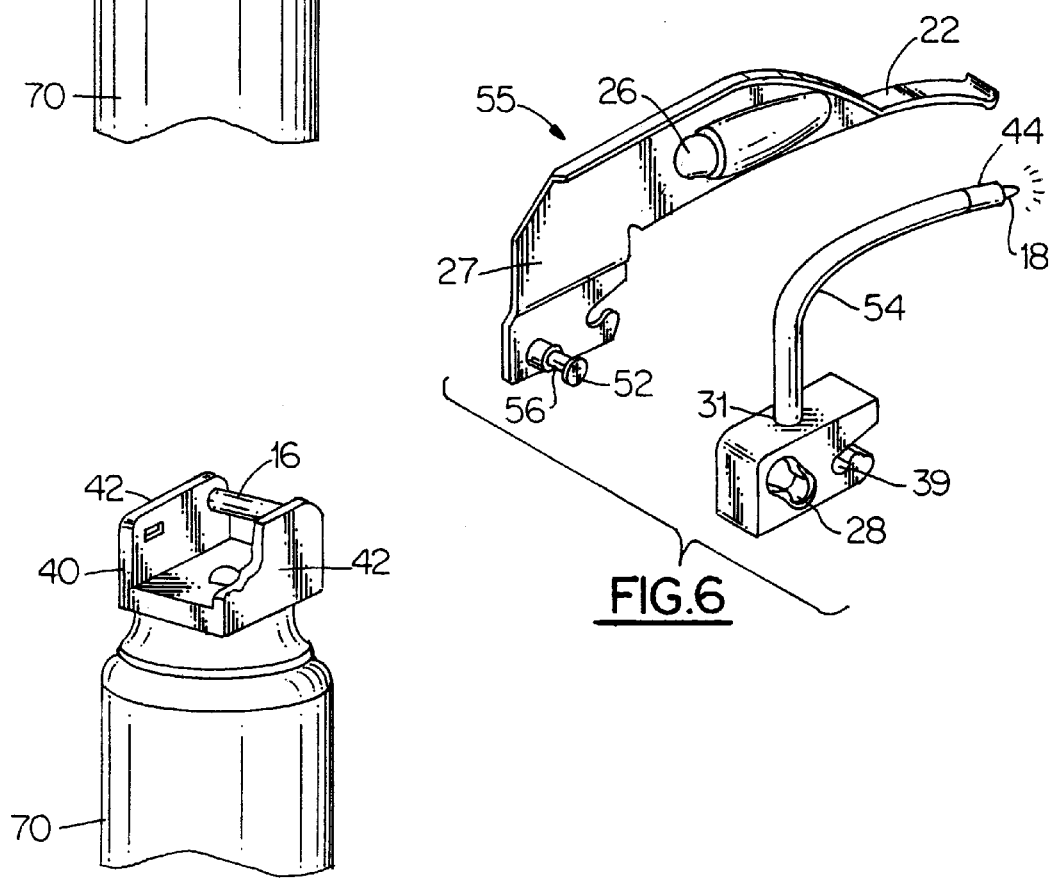
FIG. 6 is an exploded perspective view of the laryngeal blade assembly of FIG. 5.

Before describing the present invention, reference is herein first made to FIGS. 5–7 which illustrate a standard incandescent lamp laryngoscope 50. For the sake of clarity, similar parts are labeled with the same reference numerals.

The laryngoscope 50 includes a handle 70 and a laryngeal blade assembly 55 having a light pipe assembly 48 which is releasably attached thereto. The light pipe assembly 48 includes a hollow light pipe 54, but in lieu of providing a bundle of optical fibers, a halogen or other suitable miniature lamp 18 is mounted into the distal end 44 of the light pipe, the distal end being further positioned within a receiving pocket 26 provided along an interior wall 27 of the blade 22. The lamp 52 is electrically connected by a wire 62 within the hollow light pipe 54 to a contact 60 providing one side of a connection circuit with the blade 22 providing the other side of the circuit. When the laryngeal blade assembly 14 is in the operative position shown in FIG. 5, the contact 60 engages a contact button 64 which is connected to a battery power source 21 provided within the interior of the handle 70 which is urged by a spring 74 to maintain contact therewith.

The remainder of the light pipe assembly 48, however, for purposes of the present invention, is identical to that previously described including a supporting block 28 which retains a proximal end 31 of the hollow light pipe 54 in fixed relation within a top surface 30 of the block.

As clearly shown in FIGS. 5 and 7, and as in the preceding fiberoptic laryngoscope embodiment, the upper portion of the handle 70 includes a mounting bracket 40 having a pair of spaced walls 42 sized for accommodating the supporting block 28 and the blade 22 when assembled. The block 38 and a recessed proximal portion 33 of the blade 22 further includes corresponding slots 39, 38, respectively, sized to engage a pin 16 provided in the bracket 40 to provide the necessary attachment to the handle 70.

Referring to FIGS. 8–12, the bore 35 of the supporting block 28 includes a pair of contiguous receiving cavities 84, 88 which are aligned with and positioned relative to a projecting engagement member 36 of the blade 22. The first or upper receiving cavity 84 is substantially circular and is sized to adequately receive the diameter of the engagement member 36. The second or lower receiving cavity 88 includes a T-shaped slot 87 which is sized to receive the diameter of an undercut portion 56 of the engagement member 36.

Referring to FIGS. 8–12, the assembly of the light pipe assembly 24 to the laryngeal blade assembly 14 is herein described. Initially, the distal end 25 of the light pipe assembly 24 is placed into the receiving pocket 26 defined in the interior wall 27 of the blade 22. In this position, the supporting block 28 is placed in substantial proximity with the engagement member 36. The bore 35, and more specifically the circular upper receiving cavity 84 is then aligned with and fitted to the engagement member 36. Preferably, the thumb of the user is then placed on the bottom surface of the supporting block 28 and pushed in an upward direction 90, causing the undercut portion 56 to be snap-fitted within the T-shaped slot 87 of the lower receiving cavity 88.

Figure 10:
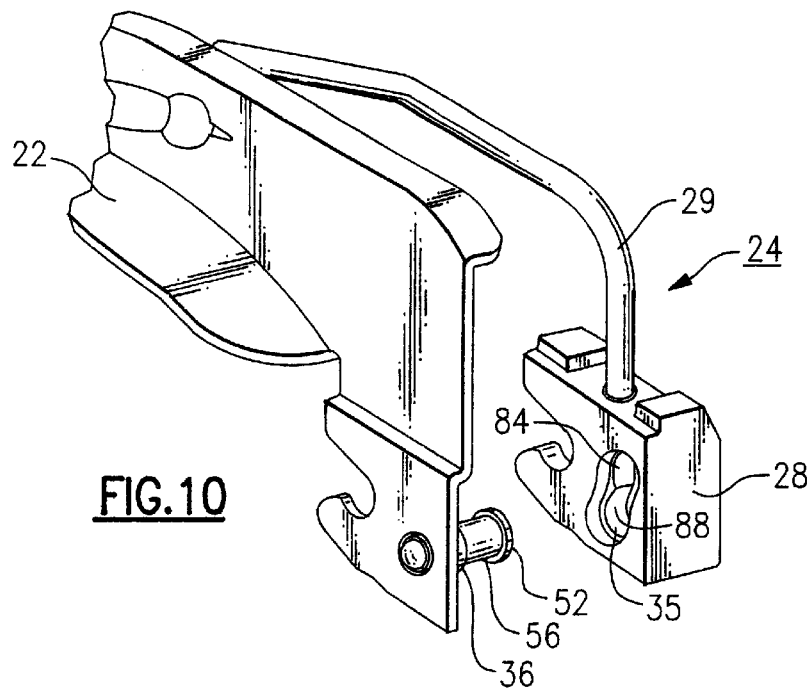
FIG. 10 is a partial side perspective view of the laryngeal blade assembly of FIGS. 8 and 9 with a light pipe assembly according to a preferred embodiment of the invention prior to attachment thereof.

After using the laryngoscope shown in FIG. 10, the blade 22 and the light pipe assembly 24 must be sanitized. Therefore, the light pipe assembly 24 must be removed from the blade assembly 14. According to the present invention, the light pipe assembly 24 can easily be released from the blade 22 by reversing the above assembly procedure and pushing the supporting block 28 in a downward direction displacing the engagement member 36 of the blade 22 into the first receiving cavity 84. The light pipe can then slid off the engagement member 36 and the receiving pocket 26 for cleaning.

In use, the light pipe assembly 24 is securely, but releasably, fastened to the laryngeal blade assembly 14. Moreover, the described attachment is adequately secure such that the light pipe assembly will not be dislodged, even if the above assembly is dropped or subjected to an impact load.

PARTS LIST FOR FIGS. 1–12
10 fiberoptic laryngoscope
12 handle
14 laryngeal blade assembly
16 pin
18 miniature lamp
19 electrical or battery contact
20 tube
21 battery power source
22 laryngeal blade
24 light pipe assembly
25 distal end
26 receiving pocket
27 interior wall
28 supporting block
29 light pipe
30 top surface
31 proximal end
32 opening
33 recessed proximal portion
35 bore
36 engagement member
37 base portion
38 slot
39 slot
40 mounting bracket
41 elongated tongue
42 spaced walls
44 distal end
48 light pipe assembly 50 incandescent lamp laryngoscope
52 cylindrical shaft
54 light pipe
55 laryngeal blade assembly
56 undercut portion
64 contact button
70 handle
84 receiving cavity
87 slot
88 receiving cavity
90 direction of movement While the present invention has been particularly shown and described with reference to certain particular embodiments, it should be readily apparent to one skilled in the art that various changes and variations are possible without departing from the spirit and scope of the invention as defined by the following claims.

I claim:

1. A blade assembly for a laryngoscope, said blade assembly comprising:

a laryngeal blade configured for viewing the larynx of a patient said blade having a primary axis;

a light pipe assembly releasably attachable to said laryngeal blade, said light pipe assembly including a light pipe and a supporting block for supporting said light pipe, said supporting block including a bore sized for receiving a non-axial engagement member extending from said laryngeal blade said engagement member being non-axial with respect to the primary axis of said laryngeal blade, said bore including a pair of adjacent substantially circular receiving cavities a first receiving cavity for initially receiving said engagement member and a contiguous second receiving cavity for releasably attaching said light pipe assembly to said laryngeal blade through subsequent sliding attachment thereto.

2. The blade assembly as recited in claim 1, wherein said engagement member includes a cylindrical shaft having an undercut portion.

3. The blade assembly as recited in claim 2, in which the first receiving cavity of the bore is sized to receive the entire diameter of the cylindrical shaft and the second receiving cavity is sized to receive only the undercut portion of the engagement member.

4. The blade assembly as recited in claim 1, wherein said light pipe assembly includes a hollow tube containing a plurality of optical light transmitting fibers.

5. The blade assembly as recited in claim 1, wherein said light pipe assembly includes a miniature lamp disposed at a distal end thereof.

6. The blade assembly as recited in claim 1, wherein said laryngeal blade is a MacIntosh blade.

7. A hand-held laryngoscope for the examination of the larynx, said laryngoscope comprising:

a handle;

a laryngeal blade attachable to said handle; and a light pipe assembly attachable to said laryngeal blade such that a light pipe is disposed along a major dimension of said blade;

said light pipe assembly including a supporting block for fixedly retaining said light pipe, said supporting block having a bore which is disposed non-axially with respect to the major dimension of said laryngeal blade, said bore being sized for receiving an engagement member of said blade and including a pair of adjacent and substantially circular receiving cavities a first receiving cavity for initially receiving said engagement member and a contiguous second receiving cavity for releasably attaching said light pipe assembly to said laryngeal blade through subsequent sliding attachment thereto.

8. The laryngoscope as recited in claim 7, wherein said engagement member has a cylindrical shaft including an undercut portion.

9. The laryngoscope as recited in claim 8, in which the first receiving cavity of the bore is sized to receive the entire diameter of the engagement member and the second receiving cavity is sized only to receive the undercut portion of the engagement member.

10. The laryngoscope as recited in claim 7, wherein said light pipe assembly includes a hollow tube containing a plurality of optical light transmitting fibers.

11. The laryngoscope as recited in claim 7, wherein said light pipe assembly includes a miniature lamp disposed at a distal end thereof.

12. The laryngoscope as recited in claim 7, wherein said laryngeal blade is a MacIntosh blade.

13. A method for releasably attaching a light pipe assembly to a laryngeal blade, said method including the steps of:

engaging a projecting member of said laryngeal blade into a bore of a supporting block of said light pipe assembly sized for receiving said member, said bore including a pair of adjacent substantially circular receiving cavities wherein said engaging step includes the step of sliding the projecting member into one of the receiving cavities; and sliding the supporting block to position the projecting member into the other of said adjacent receiving cavities of said bore to releasably lock said light pipe assembly onto said projecting member.

* * * * *